US006693427B2

(12) United States Patent
Drobnitzky et al.

(10) Patent No.: US 6,693,427 B2
(45) Date of Patent: Feb. 17, 2004

(54) HEAD COIL FOR A MAGNETIC RESONANCE APPARATUS

(75) Inventors: Matthias Drobnitzky, Spardorf (DE); Karsten Wicklow, Princeton, NJ (US)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 10/122,368

(22) Filed: Apr. 12, 2002

(65) Prior Publication Data

US 2002/0163337 A1 Nov. 7, 2002

(30) Foreign Application Priority Data

Apr. 12, 2001 (DE) .......................... 101 18 472

(51) Int. Cl.$^7$ ................................. G01V 3/00
(52) U.S. Cl. ............... 324/318; 324/322; 324/309
(58) Field of Search .................... 324/318, 322, 324/306, 307, 309, 312, 314; 600/410, 418; 128/653.5

(56) References Cited

U.S. PATENT DOCUMENTS

| 4,948,984 A | 8/1990 | Breitmeier ............... 324/318 |
| 6,298,258 B1 | 10/2001 | Heid et al. ............... 324/318 |
| 6,433,548 B1 * | 8/2002 | Furuta et al. ............ 324/318 |

OTHER PUBLICATIONS

"Giant Birefrigent Optics in Multilayer Polymer Mirrors," Weber et al., Science, vol. 287, Mar. 31, 2000, pp. 2451–2456.

* cited by examiner

Primary Examiner—Diego Gutierrez
Assistant Examiner—Brij B. Shrivastav
(74) Attorney, Agent, or Firm—Schiff Hardin & Waite

(57) ABSTRACT

A head coil for a magnetic resonance apparatus has a mirror device for the stimulation of one or both eyes with first light in a first wavelength range and for simultaneous acquisition of a eye movement with second light in a second wavelength range in a functional magnetic resonance examination. The mirror device has a mirror that reflects the first light and is transmissive for the second light or that is transmissive for the first light and reflects the second light.

28 Claims, 2 Drawing Sheets

HEAD COIL FOR A MAGNETIC RESONANCE APPARATUS

BACKGROUND OF THE INVENTION

1. Field of the Invention

The present invention is directed to a head coil for a magnetic resonance apparatus, of the type having a mirror device for the stimulation of one or both eyes with a first light in a first wavelength range and for simultaneous acquisition of a eye movement with a second light in a second wavelength range in a functional magnetic resonance examination.

2. Description of the Prior Art

Functional magnetic resonance imaging enables detection of activity in the human cortex that ensues due to an intentional stimulation. To this end, a repeated stimulus (optical, acoustic, etc.) is usually utilized, and the variation of the oxygen saturation in the blood correlated therewith is detected in images that are T2*-weighted with respect to the intensity of the signals registered with the magnetic resonance apparatus. Optical stimuli—due to the structure of clinical magnetic resonance apparatus—are made visible to the patient via an optical mirror device attached in the head coil. In some tasks, the motion of the eyeball should be simultaneously detected in order, for example, to be able to check involuntary movements as well as to be able to check the implementation of certain tasks. Further, eye movements can be utilized as feedback or even control of the stimulus presentation.

For optical stimulation, one or both eyes of the patient are illuminated with light in a first wavelength range, namely visible light. The detection of an eye movement ensues with infrared light that is emitted into one eye. The reflected infrared light is acquired with a reflected light detector and eye movement is detected on the basis of the acquisition result.

In order to be able to simultaneously supply both lights, a mirror device having two mirrors is employed, the one of which reflects the visible light supplied from outside the magnetic resonance apparatus into one or both eyes of the patient and the other reflecting the externally supplied infrared light into at least one eye. The arrangement of the two different mirrors, however, presents significant problems in practical use since the available space in the head coil is very limited. The two mirrors must be arranged such that they do not block one another, otherwise one of the light beams will not be transmitted.

German OS 198 60 037 discloses a magnetic resonance system for topically resolved measurement of the electrical activity of nerve cells. The magnetic resonance system has a magnet for generating a basic magnetic field, coils for generating magnetic gradient fields, and radio-frequency antennas for emitting and receiving radio-frequency pulses. For stimulation of neural activities of a patient to be examined with the magnetic resonance system, a pulse generator generates a stimulation function with which, for example, a light transmitter is driven for optical stimulation of the patient.

Further, German OS 37 20 079 discloses an optical sensor head for measuring the surface of a workpiece that contains an integrated microscope. To this end, a deflection mirror arranged in the wall of the housing of the sensor head is fashioned as a dielectric mirror that is opaque for measurement light and is transparent for at least one light wavelength that is not within the measurement light spectrum.

SUMMARY OF THE INVENTION

An object of the present invention is based on the problem of specifying a head coil with a mirror device wherein said difficulties in view of the arrangement are not present.

This object is inventively achieved in a head coil of the type initially described wherein the mirror device has a mirror that reflects the first light and is transmissive for the second light or that is transmissive for the first light and reflects the second light.

In the inventive mirror device, thus, only one mirror is utilized which is a dichroitic mirror, reflecting one light but allowing the other to pass. The possibility of irradiating the mirror with the light for which it is transmissive creates completely new possibilities in view of the light management. Thus, two mirrors are no longer required; on the contrary, one mirror suffices since, due to the possibility of irradiation, the respective light source can be arranged, for example, vertically above the eye region; a beam deflection can be foregone.

It is expedient when the mirror is arranged at an angle between 30° and 60°, particularly an angle of 45°, relative to the horizontal plane for reflecting a light emitted from the side and for allowing light emitted from the top to pass. One light, for example the visible stimulation light, continues to be emitted from a light source located externally from the magnetic resonance apparatus and is reflected into the eyes of the patient via the mirror, which is preferably arranged at 45° relative to the horizontal plane, whereas the second light is emitted in from above.

The mirror thus can be wide enough to extend over both eyes. Alternatively, however, two mirrors arranged next to one another and each allocated to one eye can be provided, these being capable—dependent on the design—of being charged in common or separately with the stimulation light. Expediently, the mirror device is arranged at or in a housing.

In an embodiment of the invention, a device for irradiation of the mirror is provided at the head coil above the mirror or mirrors, this device has a light source for the first light if the mirror is transmissive for this stimulation light or has a light source for the second light and an acquisition device for reflected light. According to this embodiment of the invention, thus, the respective light source, and possibly the acquisition device as well, are provided directly at the head coil. Expediently, the mirror device and the irradiation device are arranged at or in a common housing, so-that a very compact overall structural unit is achieved.

The housing can have an oblique section at which the mirror or mirrors are arranged.

The housing containing the mirror device, potentially the housing containing the irradiation device, or the housing containing both, is detachably arranged at the head coil. This makes it possible to secure the housing or the device to the head coil only when a functional MR examination is to be implemented. For normal examinations, the part is simply removed from the head coil.

In an embodiment of the invention the mirror or mirrors are fashioned as polymer mirrors. Such a mirror is electrically non-conductive, i.e. no eddy currents can arise therein—different from standard mirrors that are vapor-deposited with metal—in the magnetic fields and radio-frequency fields that are used in the MR examination. Such eddy currents can negatively influence the quality of the magnetic resonance signals. The polymer mirrors can be implemented as film, i.e. the mirror or mirrors are extremely thin; the thickness of a film lies in the range of tenths of a millimeter. Such polymer mirrors can have their reflection and transmission properties set by means of suitable selection of the polymers employed, these being arranged in various layers on top of one another. It is possible without difficulty to design a polymer mirror such that it reflects in the range of visible light between approximately 430 and 700 nm, whereas infrared light having a longer wavelength is allowed to pass.

In addition to the head coil, the invention is also directed to a magnetic resonance apparatus having a head coil of the described type.

The invention also is directed to a separate mirror device for optical stimulation of one or both eyes at the top with a first light in a wavelength range and for simultaneous acquisition of an eye movement with a second light in a second wavelength range, the mirror device being provided for detachable mounting to a head coil of a magnetic resonance apparatus. This mirror device has a housing at or in which at least one mirror is arranged, this mirror reflecting the first light and being transmissive for the second light, or being transmissive for the first light and reflecting the second light.

The mirror should be arranged at an angle between 30° and 60°, particularly at an angle of 45°, relative to the horizontal plane for reflecting a light emitted from the side—regardless of whether this is the stimulation light or the infrared light for acquiring movement—and for allowing the light emitted in from above to pass. In addition to one large-area mirror, two mirrors respectively allocated to different eyes can also be provided next to one another.

In an embodiment of the invention, a device for irradiating the mirror is provided in or at the housing above the mirrors or mirror, this device having a light source for the first light or a light source for the second light and an acquisition device for reflection light. A compact structural unit is achieved that contains all relevant components—except for an external light source and, if used, the reflection light source and, if used, the reflection light detector, dependent on which light source is integrated at the apparatus side—and that can be unproblematically secured to the head coil. The transmission properties of the mirror make it possible to provide a light source directed behind the mirror and essentially directly over the eyes of the patient in the mounted position, this light source generating light for which the mirror is transmissive. Normally, this light source would be infrared light source that additionally has an acquisition device for reflection light allocated to it on the basis of which the eye movement is acquired. An extremely compact, small-dimension unit is achieved overall that can be unproblematically secured to the head coil and which occupies extremely little space thereat.

The housing expediently has an oblique section at which the mirror or mirrors are arranged. In order to be able to secure the housing in an optimally simple way, it is expedient when a fastener enabling a plug/latch fastening or a clamp fastening of the housing to the head coil is provided at the housing.

It is also expedient when the irradiation device is displaceably arranged at or in the housing. This is expedient in order to be able to undertake an adjustment of the irradiation device with respect to the eye area of the patient as needed.

It is also expedient when displacement means are provided with which or on which the housing is displaceable relative to the head coil after being fastened to the head coil. This expedient development also serves for adjustability of the mirror device, which is displaceable overall.

The mirror or mirrors are expediently polymer mirrors, which are preferably implemented in film form.

DESCRIPTION OF THE PREFERRED EMBODIMENTS

Figure 1:
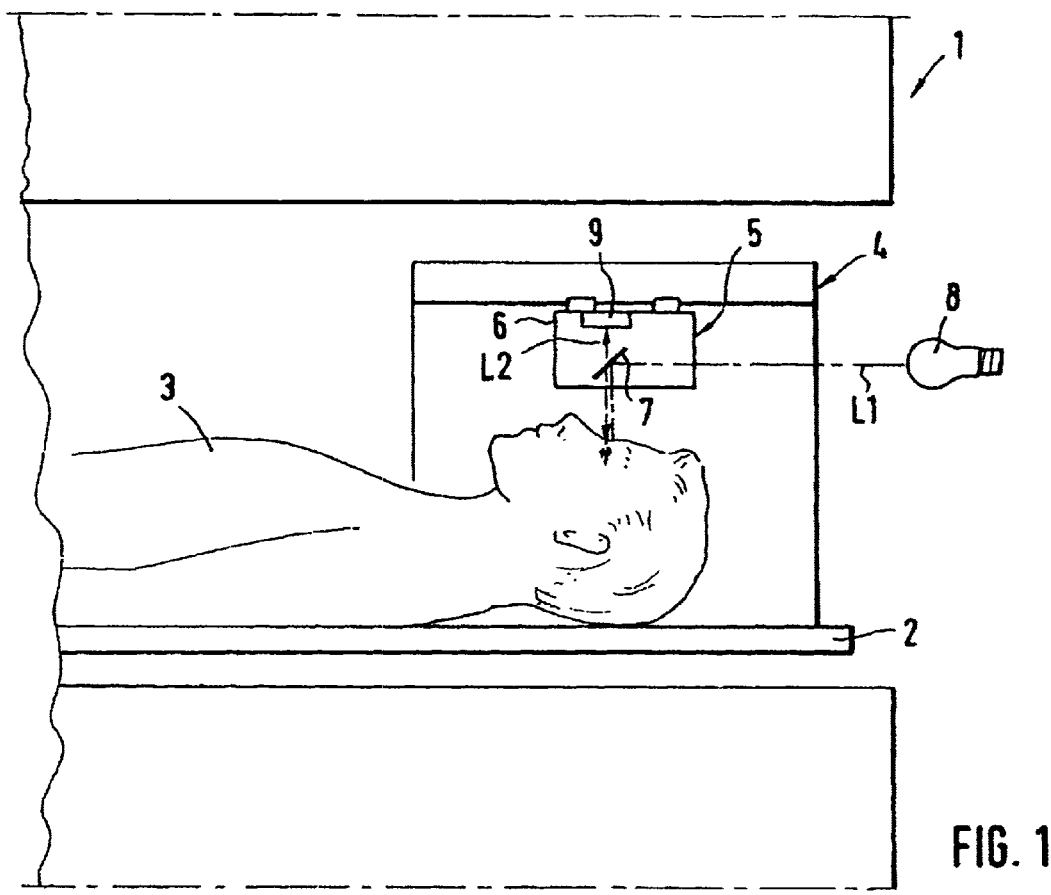
FIG. 1 is a schematic illustration of a part of an inventive magnetic resonance apparatus having an inventive head coil.

FIG. 1 shows an excerpt from an inventive magnetic resonance apparatus 1 into which a patient 3 lying on a patient bed 2 has been introduced. In the framework of a functional magnetic resonance examination, the activity or the activation behavior of the cortex in the patient 3 is to be examined given an optical stimulation of the eyes. At the same time, any eye movement must be acquired in order to be able to identify unknown or unintended eye movements that are relevant within the framework of the examination of the cortex and, as warranted, in order to be able to monitor intentional tasks to move the eyeball.

A head coil 4 is arranged around the head. As known, head coils are composed of two parts. A lower part is integrated at the patient table. 2 and is fashioned like a half-shell. Lying on his back, the patient's head is placed in this lower part of the coil. The upper coil part is removable. It can be secured to the lower part by simple plug/latch connections. Such head coils are well-known; their specific structure and functioning are of not important in the framework of the present invention.

Figure 2:
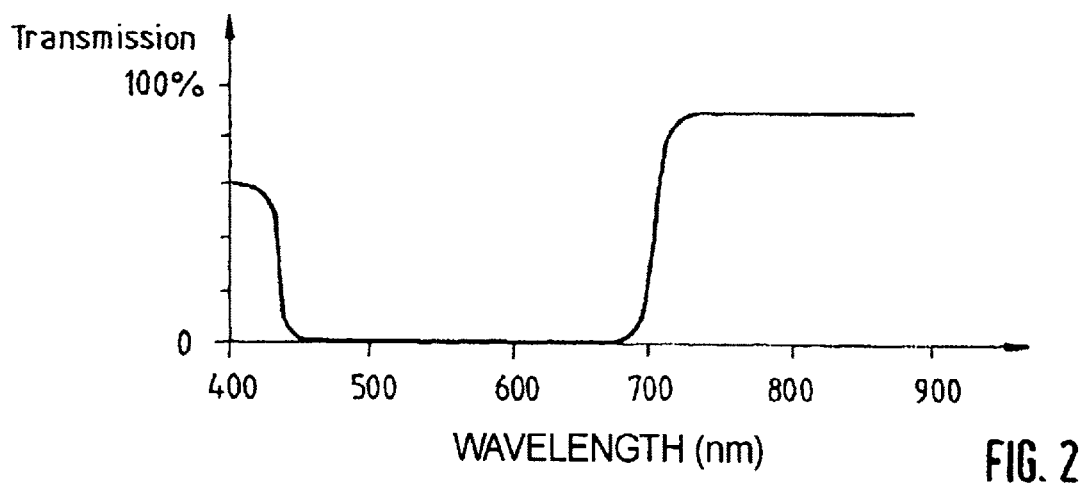
FIG. 2 is a diagram for illustrating the transmission behavior of a dichroitic mirror suitable for use in the inventive head coil.

A mirror device 5 is detachably secured to the illustrated head coil 4. The mirror device 5 has a housing 6 in which a mirror 7 is arranged at a stable position. In the illustrated example, the mirror 7 resides at an angle of 45° relative to the horizontal. The mirror 7 is a dichroitic mirror having a film structure. Such dichroitic mirrors, which are composed of various polymer plies layered on top of one another, are distinguished by a specific transmission behavior. The transmission behavior of such a mirror is shown as an example in FIG. 2. The transmission is entered in percent along the ordinate; the wavelength is entered in nm along the abscissa. As can be seen, there is no transmission in the range from approximately 430 through 690 nm. i.e., the mirror is reflective for light from this wavelength range. Beyond a wavelength of approximately 700 nm, the transmission behavior increases greatly. The mirror, by contrast, is transmissive for light in a wavelength range higher than approximately 7 nm, i.e., for infrared light.

Due to the 45° arrangement, a light stimulus can now be provided with an external light source 8 that emits visible light. The visible light is conducted onto the mirror 7 via the light path L1 shown dot-dashed, and is reflected thereat and deflected downwardly by 90° in the illustrated example. Due to the positioning of the mirror device 5 with a mirror 7 residing quasi-vertically above the eyes of the patient, the optical stimulus is reflected directly into the eyes. A housing opening or a window is provided at the end face of the housing so that the light emitted from the light source 8 can enter into the housing and strike the mirror 7.

Further, a device 9 for the acquisition of the eye movement is provided in the housing 5. This device 9, which is shown in somewhat greater detail in FIG. 3, has a second light source 10. This emits light at a wavelength that lies in the transmission range of the mirror 7. Infrared light is preferred, since this is not perceived by the human eye and consequently does not represent a stimulus since the actual stimulus should ensue exclusively with the visible light. Further, infrared light does not disturb the actual measurement. In addition, a device 11 is provided in the acquisition device 9 for acquiring the infrared light reflected by an eyeball onto which the infrared light is emitted. On the basis of this reflected light, one can detect whether the eyes carry out a voluntary or involuntary movement or not. Such methods for determining eye movements are well-known. It suffices when only one eyeball is checked for a potential movement. Due to the motion coupling of both eyes, both eyeballs are necessarily moved. Of course, it is also conceivable that such a device 9 is either allocated to each eyeball or that the device 9 is fashioned for checking both eyeballs.

The device 9 is then arranged such that it resides essentially vertically over the eyes of the patient. Infrared light is emitted via the light source 10, this being emitted along the light path L2 vertically downwardly. It passes through the mirror 7 situated under the device 9 and impinges directly into the eyes of the patient. Reflected light passes through the mirror 7 in the opposite direction along the light path L2 and in turn strikes the acquisition device 9 or the reflected light acquisition device 11.

The employment of a dichroitic mirror enables a completely new arrangement and integration of the elements required for the simultaneous implementation of the optical stimulation and the acquisition of eye movement. Due to the possibility of transirradiating the mirror with light of a specific wavelength, only one mirror is required, since the mirror no longer has any occluding effect whatsoever for light of this wavelength. Consequently, it is possible to arrange this light source behind the mirror. There is thus the possibility of integrating most of the relevant components into a small-format housing and to detachably attach this to the head coil as an auxiliary part. In addition to the embodiment with the external light source 8 shown in FIG. 1, of course, there is also the possibility of integrating this light source into the housing 5 as well.

Figure 3:
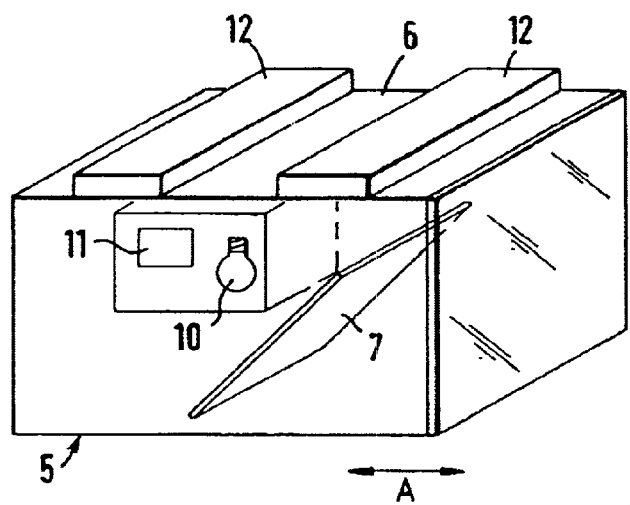
FIG. 3 is a schematic illustration of a first embodiment of a housing releasably attachable to an inventive head coil.

FIG. 3 shows the housing 5 from FIG. 1 in an enlarged illustration. The mirror 7 as noted above is a polymer mirror. Such a polymer film mirror has the advantage, since it is completely composed of plastic,—that no eddy currents are generated in it during the magnetic resonance examination, which have a negative influence on the actual magnetic resonance signals that are registered during the course of the examination of the cortex. The device 9 with its integrated components is also shown, as is a glass or plastic disk provided at the right side via which the stimulation light enters.

Further, a fastening arrangement 12 is arranged at the housing 5 shown in FIG. 3, the housing 6 being secured with the fastening arrangement 12 to the head coil 4 in a simple way as needed, or being removed therefrom. The fastening arrangement 12 is expediently fashioned as a plug/latch arrangement that can be connected to corresponding cooperating elements located at the head coil 4. A simple capability of being fastened as well as being released is important as is a secure hold. Moreover, a reproducible positional stability must also be achieved. A plug/latch fastening is not the only possible type of fastening. Of course, clamp, snap-in, screwed connections that lead to a reliable connection are also conceivable.

As described, the housing 6 can be firmly held at the head coil via the fastening arrangement 12. However, it is also required to adjust the housing with respect to the patient or the patient's eyes. Consequently, the housing is longitudinally displaceable relative to the fastening arrangement 12, as indicated by the double arrow A. This makes it possible to exactly align the housing as needed. Of course, the selected position can in turn be locked. In addition to the embodiment wherein the housing is movable relative to the fastening arrangement, of course, there is also the possibility of designing the fastening arrangement 12 such that it can in turn be movably attached to the head coil, for example on suitable displacement rails or the like. Those skilled in the art are aware of many possibilities as to how such a displaceable bearing.

Figure 4:
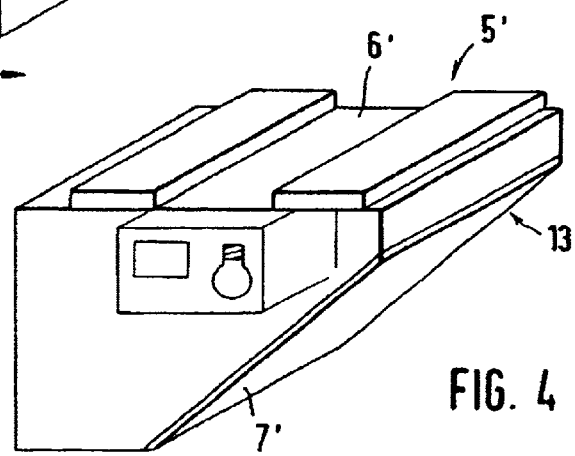
FIG. 4 illustrates a second embodiment of a housing.
Figure 5:
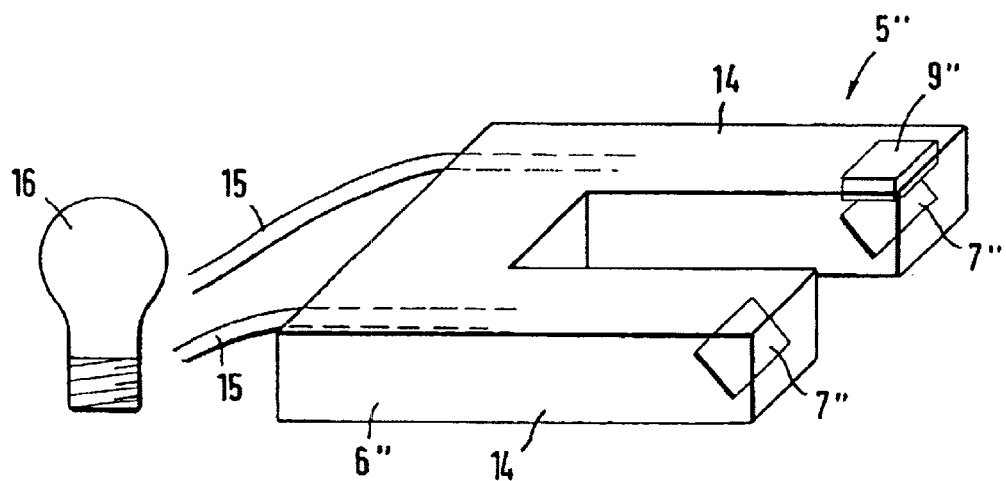
FIG. 5 illustrates a third embodiment of a housing.

FIG. 4 shows another embodiment of an inventive mirror device 5'. The components thereof are the same as described with respect to FIG. 3; it is merely the structure of the housing 6' that is different. The housing 6' has an oblique section 13. In the illustrated example, the mirror 7' is applied to this oblique section or, respectively, the slanting surface at the outside, for example by having its edge glued or the like. The mirror 7 can in turn be secured against damage from the outside via a protective covering. This makes it possible to build the mirror device 5 even smaller and to utilize the slight space available within the head coil even better.

Finally, FIG. 4 shows a further embodiment of an inventive mirror device 5". This, too, has a housing 6". Two projecting housing legs 14 are provided at the housing, respective dichroitic mirrors 7" being arranged therein. A device 9" is arranged above or behind the mirror 7" in one of the housing legs 14, serving the purpose of acquiring the eye movement. The mirrors 7" in this embodiment can be separately irradiated with visible light. To this end, suitable light guides 15 are provided to which a common light source 16 is allocated. Dependent on which light guide 15 is opened, the respectively allocated mirror 7" is irradiated. Of course, there is also the possibility of allocating a light source to each light guide 15. In addition, of course, there is also the possibility of in turn integrating the separate light sources in the housing 6". This embodiment of a mirror device thus enables the separate stimulation of one eye.

Although modifications and changes may be suggested by those skilled in the art, it is in the intention of the inventors to embody within the patent warranted hereon all changes and modifications as reasonably and properly come within the scope of their contribution to the art.

We claim as our invention:

1. A head coil for use in a magnetic resonance apparatus comprising:
   a radio-frequency coil;
   a mirror device adapted for placement in association with said radio-frequency coil relative to a head of a patient to stimulate at least one eye of said patient with a first light in a first wavelength range and for simultaneously identifying eye movement of said patient with a second light in a second wavelength range in a functional magnetic resonance examination; and
   said mirror device having a mirror which reflects one of said first light and said second light and transmits the other of said first light and second light.

2. A head coil as claimed in claim 1 wherein said mirror is disposed at an angle between 30° and 60° in said mirror device relative to a horizontal plane, and reflects said one of said of said first light and said second light proceeding to said mirror substantially parallel to said horizontal plane, and transmits the other of said first light and said second light proceeding substantially perpendicularly to said horizontal plane.

3. A head coil as claimed in claim 1 wherein said mirror is disposed at an angle of 45° in said mirror device.

4. A head coil as claimed in claim 1 wherein said mirror is a first mirror, and wherein said mirror device further comprises a second mirror, identical to said first mirror, said first and second mirrors being disposed side-by-side in said mirror device, with said first and second mirrors being respectively allocated to different eyes of said patient.

5. A head coil as claimed in claim 1 further comprising a housing for said mirror device.

6. A head coil as claimed in claim 5 wherein said housing is detachably mounted to said radio-frequency coil.

7. A head coil as claimed in claim 1 wherein said housing is displaceably mounted to said radio-frequency coil.

8. A head coil as claimed in claim 1 further comprising an irradiation device for one of said first light or said second light disposed in optical communication with said mirror.

9. A head coil as claimed in claim 8 wherein said irradiation device further comprises an acquisition device for acquiring light reflected by said mirror.

10. A head coil as claimed in claim 8 comprising a housing for said mirror device and said irradiation device.

11. A head coil as claimed in claim 10 wherein said housing has a slanted surface at which said mirror is disposed.

12. A head coil as claimed in claim 1 wherein said mirror is a polymer mirror.

13. A head coil as claimed in claim 12 wherein said polymer is formed by a polymer film.

14. A head coil as claimed in claim 1 wherein said first light is visible light and wherein said second light is infrared light.

15. A magnetic resonance apparatus comprising:
   a magnetic resonance scanner for conducting a functional magnetic resonance examination of a patient, said magnetic resonance scanner having a radio-frequency coil;
   a mirror device adapted for placement in association with said radio-frequency coil relative to a head of said patient to stimulate at least one eye of said patient with a first light in a first wavelength range and for simultaneously identifying eye movement of said patient with a second light in a second wavelength range in said functional magnetic resonance examination; and
   said mirror device having a mirror which reflects one of said first light and said second light and transmits the other of said first light and second light.

16. A mirror device for use in a magnetic resonance apparatus comprising:
   a housing adapted for placement in association with a radio-frequency coil relative to a head of a patient to stimulate at least one eye of said patient with a first light in a first wavelength range and for simultaneously identifying eye movement of said patient with a second light in a second wavelength range in a functional magnetic resonance examination; and
   a mirror at said housing which reflects one of said first light and said second light and transmits the other of said first light and second light.

17. A mirror device as claimed in claim 16 wherein said mirror is disposed at an angle between 30° and 60° relative to a horizontal plane, and reflects said one of said of said first light and said second light proceeding to said mirror substantially parallel to said horizontal plane, and transmits the other of said first light and said second light proceeding substantially perpendicularly to said horizontal plane.

18. A mirror device as claimed in claim 16 wherein said mirror is disposed at an angle of 45°.

19. A mirror device as claimed in claim 16 wherein said mirror is a first mirror, and wherein said mirror device further comprises a second mirror, identical to said first mirror, said first and second mirrors being disposed side-by-side at said housing, with said first and second mirrors being respectively allocated to different eyes of said patient.

20. A mirror device as claimed in claim 16 wherein said housing is adapted for detachable mounting to said radio-frequency coil.

21. A mirror device as claimed in claim 16 wherein said housing is adapted for displaceable mounting to said radio-frequency coil.

22. A mirror device as claimed in claim 16 further comprising an irradiation device for one of said first light or said second light disposed in optical communication with said mirror.

23. A mirror device as claimed in claim 22 wherein said irradiation device further comprises an acquisition device for acquiring light reflected by said mirror.

24. A mirror device as claimed in claim 22 comprising wherein said irradiation device is disposed in said housing.

25. A mirror device as claimed in claim 16 wherein said housing has a slanted surface at which said mirror is disposed.

26. A mirror device as claimed in claim 16 wherein said mirror is a polymer mirror.

27. A mirror device as claimed in claim 26 wherein said polymer is formed by a polymer film.

28. A mirror device as claimed in claim 16 wherein said first light is visible light and wherein said second light is infrared light.

* * * * *